United States Patent
Thompson et al.

(10) Patent No.: US 8,313,476 B2
(45) Date of Patent: Nov. 20, 2012

(54) SAMPLING NEEDLE AND METHODS OF FORMING AND USING SAME

(75) Inventors: Jeff Thompson, Los Gatos, CA (US); George N. Proper, Milpitas, CA (US)

(73) Assignee: Dionex Corporation, Sunnyvale, CA (US)

( * ) Notice: Subject to any disclaimer, the term of this patent is extended or adjusted under 35 U.S.C. 154(b) by 1250 days.

(21) Appl. No.: 11/454,076

(22) Filed: Jun. 14, 2006

(65) Prior Publication Data

US 2008/0172023 A1    Jul. 17, 2008

(51) Int. Cl.
  *A61M 5/32*   (2006.01)
  *A61B 19/00*  (2006.01)
  *A61M 31/00*  (2006.01)
  *A61M 37/00*  (2006.01)
  *A41D 19/00*  (2006.01)
  *B05D 3/00*   (2006.01)
  *B05D 7/22*   (2006.01)

(52) U.S. Cl. .......... 604/411; 604/403; 604/93.01; 604/192; 427/2.3; 427/230; 427/239

(58) Field of Classification Search .......... 604/175, 604/192, 288.02, 82, 537, 403, 411; 600/576; 422/103
See application file for complete search history.

(56) References Cited

U.S. PATENT DOCUMENTS

| | | | | |
|---|---|---|---|---|
| 4,404,862 A | * | 9/1983 | Harris, Sr. | 73/864.16 |
| 4,713,974 A | * | 12/1987 | Stone | 73/864.23 |
| 5,580,351 A | * | 12/1996 | Helgren et al. | 604/411 |
| 5,755,696 A | * | 5/1998 | Caizza | 604/164.11 |
| 5,792,217 A | * | 8/1998 | Camps et al. | 607/119 |
| 5,814,742 A | | 9/1998 | Vissers et al. | |
| 5,960,530 A | | 10/1999 | Kerr et al. | |
| 6,939,593 B2 | * | 9/2005 | Wang | 428/36.91 |
| 2002/0102185 A1 | * | 8/2002 | Tatsumi | 422/100 |
| 2003/0070278 A1 | * | 4/2003 | Chakravarti | 29/527.1 |

(Continued)

FOREIGN PATENT DOCUMENTS

DE    296 09 222 U1    10/1996

(Continued)

OTHER PUBLICATIONS

Zeus products, PEEKshrink tm—PEEK Heat Shrinkable Tubing properties. Archived copy dated Mar. 13, 2006. Accessed Apr. 16, 2008. http://web.archive.org/web/20060313112741/www.zeusinc.com/peekshrink.asp.*

(Continued)

*Primary Examiner* — Leslie Deak
*Assistant Examiner* — Adam Marcetich
(74) *Attorney, Agent, or Firm* — Morgan, Lewis & Bockius LLP; Victor E. Johnson

(57) ABSTRACT

A inert sampling needle is provided for piercing a septum of a vial containing a sample. The sampling needle includes a hollow rigid support member having an inner wall, an outer wall, and a septum-piercing end. The sampling needle also includes a sheath member affixed to the rigid support member. The sheath member covers the septum-piercing end of the support member, the inner wall, and at least a portion of the outer wall adjacent the septum-piercing end to isolate the support member from the sample. Preferably, the sheath member is formed of polyetheretherketone and is affixed to the rigid support member by heat fusing. A method of forming, and a method of using the inert sampling needle is also disclosed.

17 Claims, 4 Drawing Sheets

U.S. PATENT DOCUMENTS

2005/0217393 A1* 10/2005 Tomita et al. .............. 73/864.41

FOREIGN PATENT DOCUMENTS

| | | |
|---|---|---|
| EP | 1 143 181 A2 | 10/2001 |
| WO | WO 92/22379 A1 | 12/1992 |

OTHER PUBLICATIONS

Online encyclopedia article, "Interference fit." Accessed Apr. 16, 2008. http://en.wikipedia.org/wiki/Interference_fit.*

Online encyclopedia article, "powder coating." Accessed Apr. 16, 2008. http://en.wikipedia.org/wiki/Powder_coating.*

Van Der Vlis et al., Development of a Needle Device for On-Line Electroextraction-Liquid Chromatography, Journal of Chromatography, Aug. 9, 1996, vol. 741, No. 1, Leiden U.

Barka et al., Miniaturization of Analytical Systems, LaborPraxis, Nov. 1997, vol. 21, No. 11.

Vissers et al., A Fully Automated Microautosampler for Micro and Capillary Liquid Chromatography, International Laboratory, Jan. 1996, vol. 26, No. 1, LC Packings Int'l.

* cited by examiner

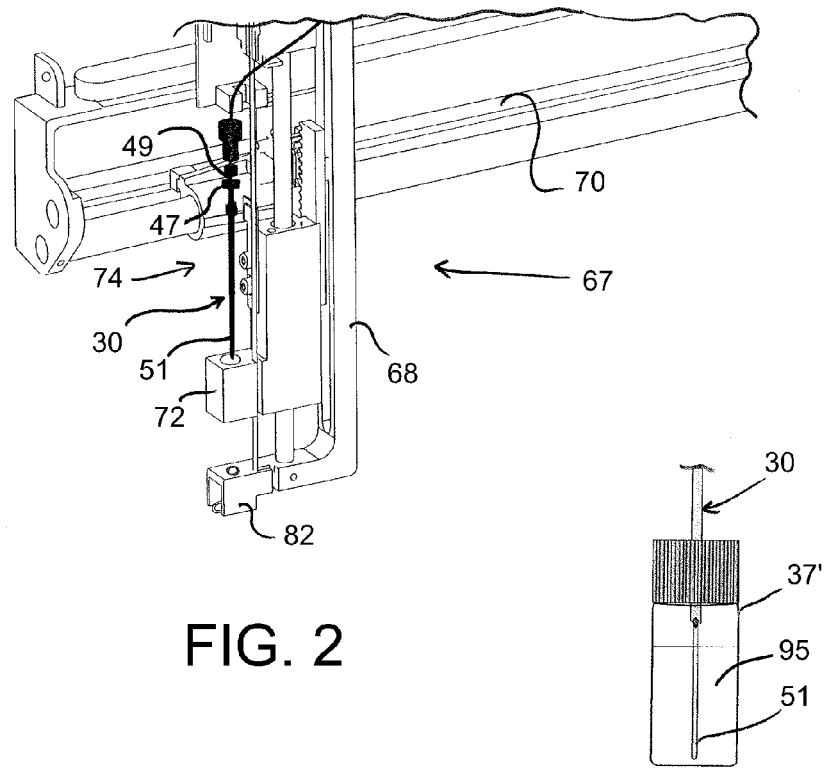
FIG. 2
FIG. 4
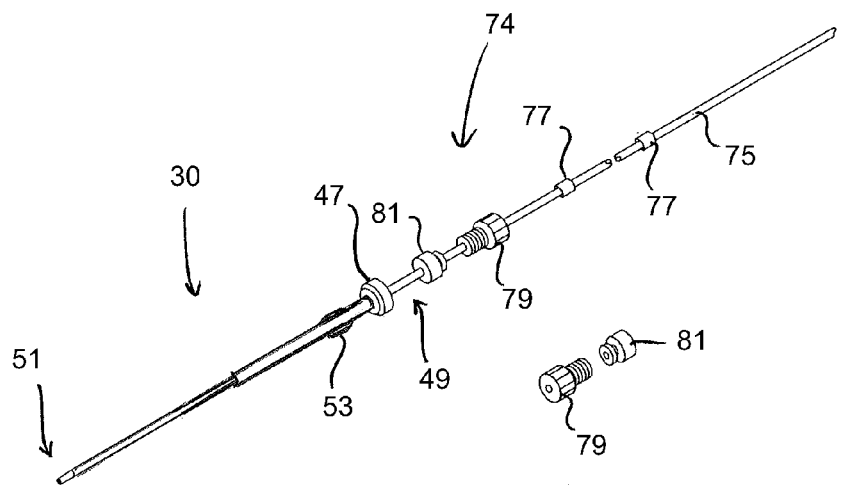
FIG. 3

SAMPLING NEEDLE AND METHODS OF FORMING AND USING SAME

TECHNICAL FIELD OF THE INVENTION

This invention relates, in general, to an inert sampling needle and more particularly to inert needles for automated columnar chromatography and methods for their manufacture and their use.

BACKGROUND OF THE INVENTION

In the fields of biochemistry and analytical chemistry, laboratory researchers generally prepare, manipulate, and analyze a multitude of samples for a variety of reasons. More recently, advances in scientific research and technology has exponentially increased the number of samples researchers can analyze. Many laboratories now employ sophisticated, automated machines able to prepare or analyze hundreds of samples at a time. Fields such as drug analysis now require unattended, automated analysis of many samples in an array as part of their standard instrumentation.

Chromatography systems often utilize a needle arm controlled by a user-defined program to analyze an array of samples in a tray. The needle arm forces the needle downward to pierce the septum or seal of a sample vial lid in the array. The needle draws in the sample and delivers it to a column. The needle must therefore have sufficient strength to repeatedly pierce sample seals and seal with injection ports.

Metal needles, however, are not desirable as "wetted" materials. Among other reasons, in order to increase reproducibility and eliminate errors, it is desirable to eliminate reactive interference by the needle material with the sample. In high-performance liquid chromatography (HPLC) applications, the metal can become corroded or interact with samples thereby diminishing system performance. Therefore, inert materials are desirable but are generally too soft to pierce a septum and cannot be used to form a needle.

One approach to this problem has been to use a strong metal to pierce the septum and a second inert material to aspirate the sample. An exemplar of this approach is the micro-autosampler described in U.S. Pat. No. 5,814,742 to Vissers et al. The Vissers autosampler discloses a sharpened metal needle and an intake tube positioned therein. In operation and use, the needle pierces a septum and the PEEK inner tube reciprocates from within the needle into the sample. The intake tube is composed of PEEK or fused silica. The metal needle has high strength and fatigue resistance, and the use of a PEEK intake tube prevents interaction between the metal and sample fluid in the needle. Although the metal needle does not directly contact the sample, the metal needle is introduced to the sample environment and vapors upon piercing the seal. Additionally, the second step of reciprocating the intake tube within the needle adds to the overall complexity of the system.

The Vissers autosampler needle also presents a problem when delivering sample fluid to an injection port. The PEEK inner tube lacks the strength to seal to an injection port. Either the stainless steel needle must be configured to seal to the port directly or an additional interface member must be utilized. This creates further complications and additional parts. It also may allow for the undesirable introduction of metal to the system if the port cannot accept the reciprocating intake tube.

Another approach has been to coat a stainless steel needle with an inert tetrafluoroethylene coating. Teflon coatings, however, may still degrade and wear off with time. With coatings, the sample may be exposed to the metal as it is drawn into the inner diameter of the needle. Furthermore, the coating may not adequately coat the needle and may be generally uneven. Uneven spots in the coating can lead to exposure of metal to the sample environment. Coated needles also need to be replaced periodically because the coatings tend to degrade and wear off with repeated use.

What is needed is a sampling needle which overcomes the above and other disadvantages. In particular, what is needed is a sampling needle with inert surfaces on the inner diameter (ID) and outer diameter (OD) of the needle able to withstand repeated use and having sufficient strength to pierce septa and seal to injection ports.

BRIEF SUMMARY OF THE INVENTION

In summary, one aspect of the present invention is directed to providing a sampling needle for piercing a septum of a vial containing a sample, the needle including a hollow rigid support member having an inner wall, an outer wall, and a septum-piercing end, and a sheath member affixed to the rigid support member. The sheath member covers the septum-piercing end of the support member, the inner wall, and at least a portion of the outer wall adjacent the septum-piercing end to isolate the support member from the sample.

In one embodiment, the sheath member covers most of the outer wall. The sheath member may include concentric cylinders interconnected by a crowning member, the crowning member being adjacent the septum-piercing end of the support member. The sheath member may include another crowning member interconnecting the concentric cylinders adjacent another end of the support member remote from the septum-piercing end. In another embodiment, an outer one of the concentric cylinders is segmented. The sheath member isolates the septum-piercing end of the support member from the environment.

In one embodiment, the sheath member is formed by extrusion. The crowning member may have a thickness substantially equal to the combined wall thicknesses of the extruded cylinders and the support member.

In one embodiment, the sheath member is secured to the support member with an interference fit. The sheath member may also mechanically capture the support member or mechanically crimp to the support member.

The sheath member is formed of an inert material. The sheath member may be a plastic, such as polyetheretherketone or a heat-shrinking plastic, or other suitable inert materials. In one embodiment, the support member is stainless steel.

The sampling needle is used in combination with a vial having a lid with a piercable septum. The needle is configured to pierce the septum and retract from the In one embodiment, the method of forming the sampling needle includes one or more of the following steps: providing a rigid needle having an insertion portion configured for piercing a vial seal, providing an inner tube of inert material and inserting the inner tube through an inner diameter of the needle, providing an outer tube of inert material and affixing the outer tube to the needle, and interconnecting the inner tube and outer tube to form an integral sheath member. The sheath member encloses the insertion portion and seals an internal wall of the needle from the environment.

In one embodiment, the interconnecting step is accomplished by fusing together the inner tube and the outer tube by heat. At least one of the inner tube and outer tube may be formed by extrusion.

In one embodiment, the inner and outer tubes of inert material are affixed to the needle by an interference fit. The inner and outer tubes of inert material may also be affixed to the needle by heat shrinking, mechanical crimping, mechanical capturing of the rigid needle, or other methods.

In one embodiment, the sheath member is configured for repeated piercing of the seal and for repeated sealing to an injection port. The sheath member may be formed of a polyetheretherketone and other suitable inert materials. The needle may be formed of stainless steel and other suitable materials.

In one embodiment, the method of using the sampling needle includes one or more of the following steps: providing a solution in a vial having a lid with a septum, providing a needle having a rigid support member and an inert sheath member, the sheath member being configured to cover and isolate a septum-piercing end of the rigid support member from the solution in the vial, piercing the septum with the needle, drawing the solution into the needle, and retracting the needle from the vial. The solution is isolated from the needle.

In one embodiment, the piercing, drawing and retracting steps are performed repeatedly. The method of using the needle may further include expelling the solution into a separation column through an injection port.

In one embodiment, the sealing step is accomplished by sealing to an injection port operably connected to an injection valve and chromatography column of a chromatography system. The method may further include the step of sealing another end of the needle remote from the septum-piercing end to a fluid-moving device or pump.

The inert sampling needle of the present invention has other features and advantages which will be apparent from or are set forth in more detail in the accompanying drawings, which are incorporated in and form a part of this specification, and the following Detailed Description of the Invention, which together serve to explain the principles of the present invention.

BRIEF DESCRIPTION OF THE DRAWINGS

FIG. 2 is an enlarged perspective view of a needle control system movably mounting the sampling needle of FIG. 1 within the chromatography system of FIG. 1.

FIG. 3 is an enlarged perspective view of a needle assembly including the sampling needle of FIG. 1.

FIG. 4 is a side view of the inert sampling needle of FIG. 1 inserted into a sample vial in accordance with the present invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

For convenience in explanation and accurate definition in the appended claims the detailed description, the terms "up" or "upper", "down" or "lower", "inside" and "outside", "fore" or "forward" and "aft" are used to describe features of the present invention with reference to the positions of such features as displayed in the figures.

Figure 1:
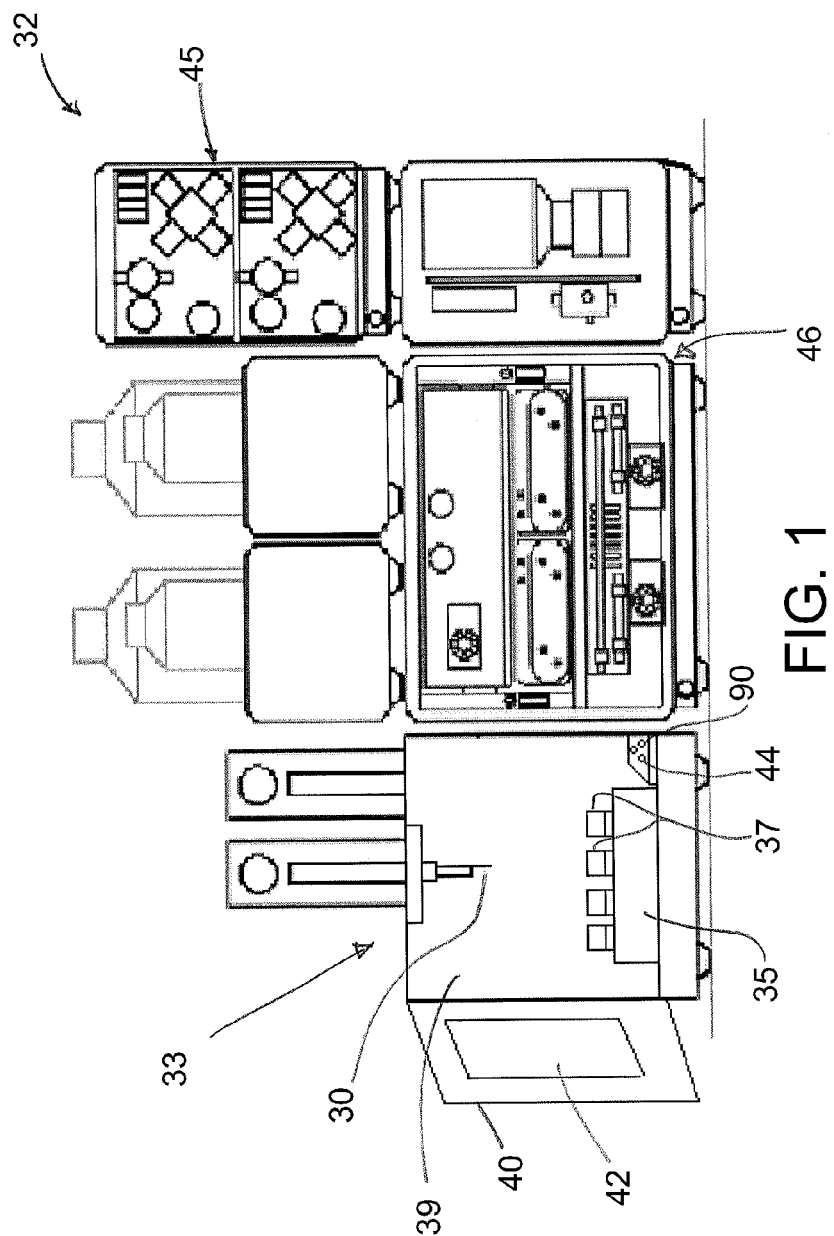
FIG. 1 is a perspective view of an autosampler and chromatography system utilizing a sampling needle having inert surfaces in accordance with the present invention.

Turning now to the drawings, wherein like components are designated by like reference numerals throughout the various figures, attention is directed to FIG. 1 which illustrates an inert sampling needle 30 in accordance with the present invention. In the illustrated embodiment, the sampling needle is part of chromatography system 32, and more particularly part of an autosampler system 33 of similar type to the AS Autosampler currently sold by Dionex Corporation of Sunnyvale, Calif. While the illustrated system is used for ion chromatography (IC) or high-pressure liquid chromatography (HPLC) applications, one will appreciate that the inert sampling needle can be used with a number of detection and preparation apparatus and methods including, but not limited to, other forms of chromatography, conductometry, thermal conductivity, and other laboratory or industrial sampling applications. In general, the inert sampling needle of the present invention may be used for any manual or automated, non-contact sample delivery application.

In the illustrated embodiment shown in FIG. 1, an IC system includes autosampler system 33. The autosampler system also includes a sample tray 35 holding an array of sample vials 37, a sample compartment 39 with a door 40 having a window 42, and flush, waste, and inject ports generally designated by the numeral 44. The autosampler system is operably connected to a chromatography device 46, such as a detector/column module, and pumps 45. In operation, the array of sample vials are placed into the sample compartment. The user closes the door and sets the desired program using computer controls to execute a program such that the automated sampling needle configuration provides samples from the sample vials to the chromatography device without any further user control or input.

Turning now to FIG. 2 and FIG. 3, inert sampling needle 30 is shown with a fitting or mounting stop 47 adjacent an attachment end 49. The stop may be a fitting, nut, protrusion, or other component known in the art. At an opposite end, a septum-piercing end 51 is configured for piercing a septum on a vial lid and insertion into the vial (see, e.g., FIG. 3). Although sampling needle 30 is depicted with a substantially tubular shape, one will appreciate that the shape and cross-section may vary. Intermediate the ends, the sampling needle includes a venting structure 53 to promote the drawing of sample fluid from the vials.

Vial 37' includes a septum to prevent contamination and reduce evaporation, and the subsequent change in concentration, of the sample. Vial septa generally are solid films sealed to the top edges of the vial. As known in the art, the septa may also have a split configuration, either partial or full, to reduce the force required for piercing while still protecting the sample environment.

Figure 5:
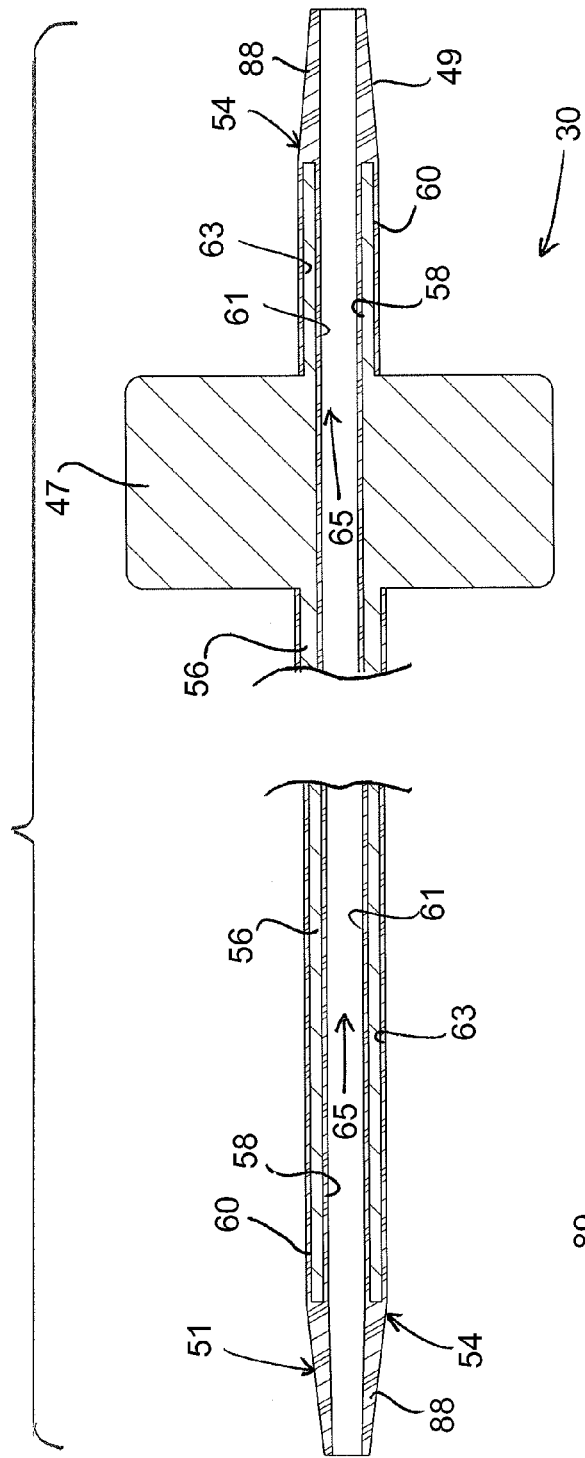
FIG. 5 is an enlarged cross-sectional side view of the sampling needle of FIG. 1.

With reference to FIG. 5, the needle includes an inert sheath member 54 wrapped around a rigid support member 56. It is highly desirable to completely eliminate exposure of metallic and or non-inert parts of the sampling needle and other components of the system from the sample. Accordingly, sheath member 54 extends along an inner wall 58 and outer wall 60 of the needle to isolate the rigid support member from the sample. In contrast to coatings, the sheath member is a discrete member affixed to the support member rather than a material adhered to the support member. In the illustrated embodiment, the inner and outer walls have a cylindrically tubular shape. One will appreciate that the shapes may vary depending on the application. For example, the sheath member may have a conical shape with tapering inner and outer walls or non-laminar walls.

In the illustrated embodiment, the inner and outer walls of the sheath member extend beyond and cover septum-piercing end 51 of the support member, as well as the attachment end 49. One will appreciate, however, that other configurations may be used and there may be other configurations which do not require the attachment end be enclosed by the sheath, for example, when the flow path of the needle does not extend to and/or through the attachment end of the needle.

Sheath member 54 fully encloses support member 56 such that septum-piercing end 51 of support member 56 is prevented from contact with the environment. In the illustrated embodiment, the sheath member also includes an inner cylindrical portion 61 which isolates the inner wall 58 of support member 56 from the environment, and an outer cylindrical portion 63 of sheath member 54 which isolates a majority of the outer wall 60 of the support member from the environment. In the illustrated embodiment, the inner and outer cylindrical portions have substantially equal and uniform thicknesses. One will appreciate, however, that the thicknesses of the cylindrical portions need not be uniform or equal with one another. At the piercing end, sheath member 54 completely covers support member 56 to prevent contact with the sample when needle 30 is submerged in the sample.

Fluid is drawn into or expelled from the needle along a flow path 65 largely defined by the inner wall of the support member. Thusly, the sheath member and mainly the inner cylindrical portion 61 thereof prevents fluid flowing along the flow path of the needle from coming into contact with the support member. In the illustrated embodiment, the sheath member fully coats inner wall 58 to prevent contact of an inner wall of support member 56 with flow path 65. One will appreciate that other configurations may be used to isolate the support member depending on the particular application.

In the illustrated embodiment, sheath member 54 is formed of polyetheretherketone (PEEK), and the support member 56 is formed of stainless steel. In this embodiment, PEEK has been chosen for its non-reactivity and good mechanical properties, while stainless steel has been chosen for its rigid mechanical properties and general structural integrity. One will appreciate, however, that other suitable materials may be used. The sheath member may be any inert material or composite including, but not limited to, inert plastics, polyetherketones, and other suitable inert materials. The sheath member may also be any material from the TEFLON family of polymers such as PolyTetraFluoroEthylene (PTFE) and PerFluoroAlkoxy polymer (PFA) and Fluorinated Ethylene Propylene (FEP), TEFZEL or Ethylene TetraFluoroEthylene (ETFE), KEL-F or PolyChloroTriFluoroEthylene (PCTFE), poly methyl pentene (TPX), Ultra High Molecular Weight polyethylene (UHMWPE), Polypropylene, Polyphenylene Sulfide (PPS), polyimide, a variety of Liquid Crystal Polymers (LCP), other inert polymers, and the like. The sheath member material depends on the application, but generally the material should be non-reactive with the sample, which may contain ionized aqueous solutions, acids and bases, or organic compounds. The choice of sheath material also depends on the nature of the material to be separated and the end results desired. The support member may be any rigid material including, but not limited to, metal-alloys and metals such as steel, stainless steel, aluminum, copper, and zinc and ceramics, rigid plastics, rigid thermoplastics, composites, combinations thereof, and/or other suitable materials.

In one embodiment, the stop 47 is rigidly mounted to the support member and may be formed of any suitable rigid material. In another embodiment, the stop is mounted to the support member by a friction fitting. The fitting slips over the support member by interference fit and is then clamped down to the support member or supported by a movable crimp. The use of such a friction fitting allows the sheath member to extend the full length of the support member.

In the illustrated embodiment, septum-piercing end 51 of sheath member 54 has tapering edges to facilitate puncturing or piercing a seal of a sample vial. One will appreciate that other shapes may be used including, but not limited to, a serrated edge or a rising blade edge.

Returning to FIG. 2, a sampling needle control system, generally designated 67, is shown. The needle control system includes a sampling needle arm 68, commonly referred to as a z-arm, that is operably mounted on a track arm 70, commonly referred to as a needle x-y arm. The needle arm includes a reciprocating needle block 72 which receives needle assembly 74 such that the needle assembly reciprocates up and down. The needle assembly includes sampling needle 30, as well as a flexible transfer line tubing 75, sleeves 77 to allow the flexible tubing to be captured and located during arm motions without crimping the tubing, and fittings (e.g., bolt 79 and ferrule 81) to mount the sampling needle and connect to the transfer line tubing in an otherwise conventional fashion.

The needle assembly is assembled in a conventional fashion in which needle 30 slides through needle block 72 until mounting stop 47 seats properly within the needle block, and with respect to a needle guide 82. Among other functions, the guide serves to support the needle. A proximal free end of the tubing is affixed to the needle with ferrule 81 while a remote free end of the tubing extends outside the sample compartment to the appropriate device. In one embodiment, the underside of the guide includes a sensor that determines when the top of the vial abuts the guide.

The sampling needle of the present invention may be manufactured in a variety of ways. The manufacturing process for forming sampling needle 30 generally involves multiple steps. Firstly, a rigid needle or support member 56 with a septum-piercing end 51 is provided which serves as a base component of sampling needle 30. A mounting stop 47 that allows the needle to be mounted rigidly in the needle control system is affixed to the support member. The mounting stop may be mounted by welding, adhesive, or other suitable mounting and fastening means.

Next, sheath member 54 is affixed to the support member and forms inner and outer wall surfaces that protect the support member from the environment and isolate the support member from the samples and other fluids which may pass through the sampling needle.

In one embodiment, sheath member 54 is formed from multiple extrusions. A first extrusion forms an inner tube, that is, inner cylindrical portion 61. The inner tube has an outer diameter substantially equal to an inner diameter of the support member. A second extrusion forms an outer tube, that is, outer cylindrical portion 63. The outer tube has an inner diameter substantially equal to an outer diameter of the support member. The inner tube is inserted into and preferably through the support member, and is affixed to inner wall 58 of the support member by an interference fit.

Similarly, an outer tube is slid over the support member and is affixed to outer wall 60 of the support member by an interference fit. In the illustrated embodiment, two outer tubes are slid over the support member, a respective outer tube being slid over each end of the support member such that inner ends of the outer tubes abut against mounting stop 47, thereby substantially enveloping the outer wall 60 of the support member. Alternatively, a single outer tube is slid over the entire length of the support member, provided that the outer tube has enough "give" and resilience to pass over stop 47, or in instances where the needle does not have such a fitting, stop, or a friction-fit stop. In yet another embodiment, the outer tube extends the length of the support member and a friction-fit stop mounts over the outer tube.

In another embodiment, the sheath member and support member are formed separately as a discrete components. The sheath member is dimensioned to capture the support member. The support member is inserted into and captured by the sheath member. The support member and sheath member may be affixed to one another by means known in the art.

Figure 7:
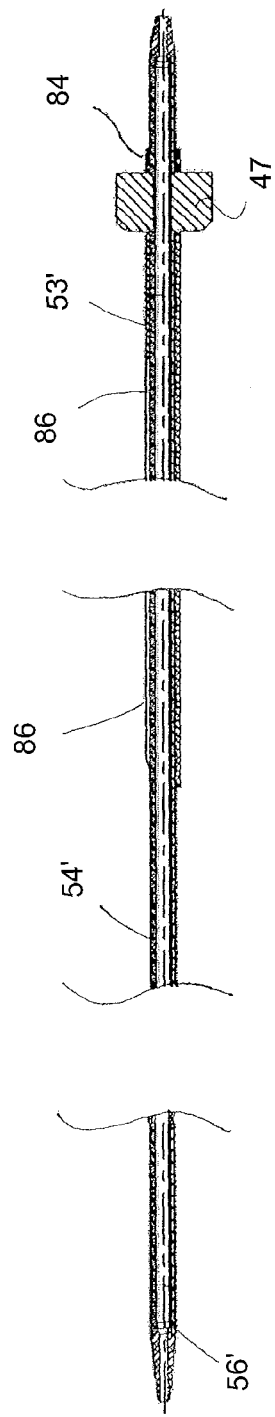
FIG. 7 is an enlarged cross-sectional view of another embodiment of a sampling needle in accordance with the present invention, the sampling needle shown with the sheath member crimped to the support member.

Turning to FIG. 7, another embodiment of the needle assembly in accordance with the present invention is shown. The needle assembly includes a crimp collar 84 at an upper end above stop 47 and a crimp support 86 at a lower end. Subsequent to assembly of the needle assembly as described above, the crimp collar and support are crimped. The crimp collar and support are configured to allow crimping of sheath member 54' to support member 56' without piercing the sheath member. The crimp force should not be so great as to damage the sheath member and the support member.

In the illustrated embodiment, the crimp support includes vent 53' internal to the member. Thus, the crimp support is of sufficient length to ventilate the inside of the vial to the ambient environment when the needle assembly is sealed to the vial. A lower end of crimp support 86 may be tapered, rounded, or otherwise shaped to enhance piercing of septa. One will appreciate that other configurations may be used as known in the art to affix the sheath member to the support member. The crimp support and collar may have alternative shapes depending on the application.

One will appreciate that other suitable means for affixing the inner and outer tubes to the support member may be used including, but not limited to, slip-fitting, heat-shrinking, adhesives, sonic welding, or using other crimping means. It is also possible to affix the inner and outer tubes to the support member only at the two ends. The inner and outer tubes may alternatively be free from the support member except at each end. It is also possible to fuse the inner and outer tube at each end effectively capturing the support member between the two fused ends. In this case the support member pushes on the septum-piercing end of the two fused tubes but is not affixed.

In the illustrated embodiment, the inner tube and outer tube have substantially equal wall thicknesses in the range of approximately 0.001-0.003 inches, however, one will appreciate that the tubes can have thicknesses less than or greater than this range. Moreover, the tubes do not need to have equal thicknesses. Although in the illustrated embodiment the tubes are extruded, other suitable fabrication methods may be used including, but not limited to, injection molding and stretch forming.

Figure 6:
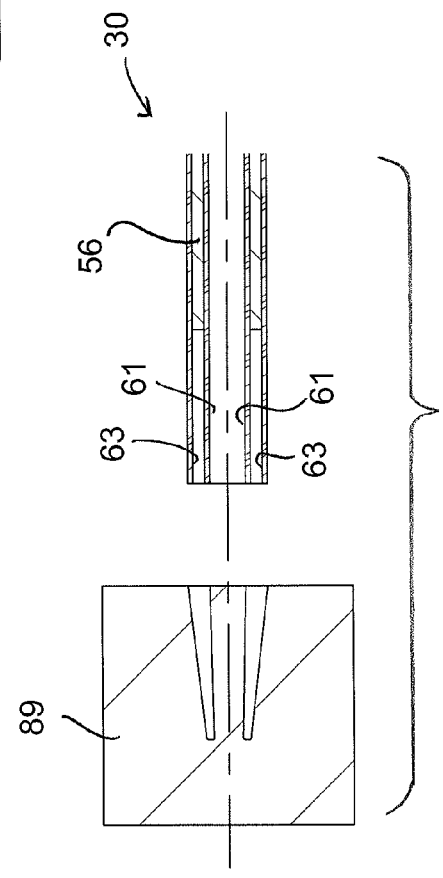
FIG. 6 is an enlarged cross-sectional side view illustrating a method of forming the sampling needle of FIG. 1.

Turning again to FIGS. 5-6, the inner and outer tubes are next cut to length. In the illustrated embodiment, the inner tube has a length slightly greater than the length of the support member whereby both ends of the inner tube extend beyond the ends of the support member. In this embodiment, the sheath member covers most of the support member such that the outer surface of the support member is not exposed. In the illustrated embodiment, the combined length of the outer tube (or the length of the outer tube) is substantially equal to the inner tube. One will appreciate that the cutting to length may be done prior to inserting and/or sliding the tubes into and/or onto the support member. The relative lengths of the inner and outer tubes may also vary depending on the application.

Thereafter, at least the respective ends of the inner and outer tubes proximal septum-piercing end 51 of support member 56 are interconnected to form a crowning member 88 integrally interconnecting inner tube 61 with outer tube 63, as shown in FIG. 5. Thus, a single, integral member is formed which completely encloses the septum-piercing end of the support member. Similarly, the ends of the inner and outer tubes proximal attachment end 49 of the support member may similarly be interconnected with a crowning member. In one embodiment, the inner and outer tubes are heated and melded or welded together to form the tip of sampling needle 30. A heated die 89 (FIG. 6) may be used to both heat up the ends of the inner and outer tubes and to provide crowning member 88 with its ultimate shape. Alternatively, the inner and outer tubes may be integrally joined, and the crowning member integrally formed, by other means including thermoforming, sonic welding, mechanical compression-sealing, machining and other suitable means.

The configuration of the present invention, namely, the integrally interconnected inner and outer tubes and crowning member assures full isolation of the septum-piercing end of the needle and other portions of the needle that may come into contact with samples and/or other fluids. In contrast to coating and other prior methods, the crowning member has a significant dimensional thickness and sufficient structural integrity to withstand repeated contact with septa and sealing to an injection port 90. In the illustrated embodiment, the crowning member has a thickness substantially equal to the combined wall thicknesses of the support member and the inner and outer walls. One will appreciate, however, that the wall thickness of crowning member may vary within the scope of the present invention.

In the illustrated embodiment, the formed end of the inner and outer tubes, that is, the crowning member 88 has a tapered shape to facilitate piercing of septa and sealing to the injection port. The integral sheath member extends beyond the support member sufficiently to prevent contact with the environment but does not extend beyond where it lacks support from the support member. The septum-piercing end thus formed is configured for repeated piercing and insertion through septa without fatigue-failure.

One will appreciate that the inner tube and outer tube dimensions may vary according to the desired configuration of sheath member 54. For example, the outer tube or inner tube may be shorter than the sampling needle provided that they have a length greater than the intended submersion depth of sampling needle 30 in the samples. One will also appreciate that the inner and outer tubes do not have to be equal in length or thickness. Various lengths and thicknesses may be employed, but the dimensions should be sufficient to prevent the support member from contacting the sample environment. The dimensions should also be sufficient to allow the material to withstand repeated contact with septa.

Turning now to operation and use, attention is directed to FIG. 1. The sampling needle 30 generally is used to move fluids between sample tray 35 and ports 44. A step motor, solenoid, or other suitable driving system positions needle arm 68 above sample tray 35 and above ports 44 in a conventional fashion. The needle arm slides along the track, and needle block 72 lifts and lowers needle assembly 74.

The basic operation for a columnar chromatography system utilizing a sampling needle in accordance with the present invention will be described herein. Autosampler 33 includes ports 44 into which sample is provided. Syringe drives and switching valves provide fluid flow into and out of the sampling needle.

Before contacting the sample, sampling needle 30 is generally primed. Sampling needle 30 is lowered into a waste port. The syringe drive and valve aspirates flush or prime fluid from a reservoir into the syringe. In the illustrated embodiment, the syringe and valve are sufficient to control the flow of fluid. One will appreciate that a check valve or other known devices may also be used to regulate the fluid flow and prevent backflow. The syringe valve switches from the reservoir to the needle and dispenses flush or prime fluid from the syringe through the sampling needle into the waste port. The needle is then positioned above ports 44 lowered to a waste port 91 where it expels the waste wash fluid. Next, the sampling needle is engaged with a flush port 93. The flush port contains fluid for washing the outside of the needle with fluid from a flush reservoir. Any spillover will fall into waste port 91. After the needle is washed, flush wash is drawn into the needle. The needle then seals to and injects flush wash into the injection port 90.

The needle assembly then slides along the track to a desired position above a sample. As illustrated in FIG. 4, the needle is lowered into a sample vial 37' whereby the lower insertion portion of the needle pierces a septum of the vial. The needle assembly is driven downward by application of force onto mounting stop 47 affixed to the support member. The needle is lowered a sufficient distance such that the insertion portion of the needle comes close to but does not touch the bottom of vial 37'. In this position, the needle tip is submerged in sample 95 without contacting the vial. Vent 53 lies above the sample to promote the drawing of sample fluid. In the illustrated embodiment, the mounting stop also serves to counter forces applied to crimp support 86 when piercing septa. One will appreciate that other configurations known in the art may be used to apply force to the support member while minimizing force on the sheath member.

After the sample is aspirated, sampling needle 30 is moved to align with and seal with an inject port 44 in an otherwise conventional fashion. The inject port is connected to an injection valve and column configured for the chromatography process, and/or with other suitable analysis devices. The needle and tubing are then rinsed and washed in a similar manner as described above.

The sampling needle of the present invention has several advantages over prior art systems. The sheath member of the present invention provides a constant, substantially-uniform, resilient coating for the rigid support member. In contrast to the prior art, the sheath member does not have any gaps or holes exposing the support member to the environment that typically occurs with spray-on coatings.

After repeated applications, coatings that are sprayed or brushed to the surface of the needle tend to rub off and thin. Prior art needles must therefore be replaced periodically. Because the sheath member is formed from separate tube structures with thickness, it has superior strength and fatigue-resistance to prior art coatings.

Furthermore, coatings and other prior art methods generally do not provide sufficient coating of the septum-piercing end of the needle and provide no structural integrity to the septum-piercing end of the needle. They also lack the rigidity to seal to an injection port. In contrast, the crowning member of the sheath member fully insulates the septum-piercing end and provides some degree of structural integrity.

Additionally, the independently-formed sheath member has good strength characteristics at the septum-piercing end of the support member. Thus, the tip of the sheath member can withstand repeated contact with septa and an injection port without exposing the inner support member to the septa or samples.

One will appreciate that the sampling needle of the present invention may be used in a variety of other applications. In general, the needle may be used in any application where a multitude of samples are aspirated and moved within an array or larger system in any laboratory or industrial application environment.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A sampling needle for piercing a septum of a vial containing a sample, the needle comprising:
 a hollow, rigid support member having an inner wall, an outer wall, and a septum-piercing end; and
 a sheath member affixed to the rigid support member, wherein the sheath member covers the septum-piercing end of the support member, the inner wall, and at least a portion of the outer wall adjacent the septum-piercing end to isolate the support member from the sample while piercing the septum and aspirating the sample.

2. The sampling needle of claim 1, wherein the sheath member covers most of the outer wall.

3. The sampling needle of claim 1, wherein the sheath member mechanically captures the support member.

4. The sampling needle of claim 1, wherein the sheath member is mechanically crimped to the support member.

5. The sampling needle of claim 1, wherein the sheath member is formed of an inert material.

6. The sampling needle of claim 5, wherein the inert material is plastic.

7. The sampling needle of claim 6, wherein the inert material is a polyetheretherketone.

8. The sampling needle of claim 1, wherein the support member is stainless steel.

9. The sampling needle of claim 1 in combination with a vial having a lid with a pierceable septum, wherein the needle is configured to pierce the septum and retract from the vial.

10. The sampling needle of claim 9 in combination with a chromatography system having an array of sample vials and an injection port, wherein the needle is configured to pierce septa on the sample vials and seal to the injection port.

11. A sampling needle for piercing a septum of a vial containing a sample, the needle comprising:
 a hollow, rigid support member having an inner wall, an outer wall, and a septum-piercing end; and
 a sheath member affixed to the rigid support member, wherein the sheath member covers the septum-piercing end of the support member, the inner wall, and at least a portion of the outer wall adjacent the septum-piercing end to isolate the support member from the sample while piercing the septum, wherein the sheath member comprises concentric cylinders interconnected by a crowning member, the crowning member being adjacent the septum-piercing end of the support member.

12. The sampling needle of claim 11, wherein the sheath member includes another crowning member interconnecting said concentric cylinders adjacent another end of the support member remote from the septum-piercing end.

13. The sampling needle of claim 11, wherein the sheath member isolates the septum-piercing end of the support member from environment.

14. The sampling needle of claim 11, wherein the sheath member is formed by extrusion.

15. The sampling needle of claim 14, wherein the crowning member has a thickness substantially equal to the combined wall thicknesses of the extruded cylinders and the support member.

16. The method of claim 11, wherein the crowning member is formed by heat fusing the concentric cylinders.

17. The method of claim 11, wherein the concentric cylinders are affixed to the needle by an interference fit.

* * * * *